United States Patent
Nelson et al.

(10) Patent No.: US 10,246,391 B2
(45) Date of Patent: Apr. 2, 2019

(54) METHOD OF RECOVERING PHENOL FROM A BPA PRODUCTION FACILITY AND THE FACILITY FOR RECOVERING THE SAME

(71) Applicant: Sabic Global Technologies B.V., Bergen op Zoom (NL)

(72) Inventors: Mark Erik Nelson, Mt. Vernon, IN (US); Ahmed Abouelfetouh Youssef, Mt. Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/757,070

(22) PCT Filed: Nov. 22, 2016

(86) PCT No.: PCT/IB2016/057024
§ 371 (c)(1),
(2) Date: Mar. 2, 2018

(87) PCT Pub. No.: WO2017/093847
PCT Pub. Date: Jun. 8, 2017

(65) Prior Publication Data
US 2018/0258020 A1  Sep. 13, 2018

Related U.S. Application Data
(60) Provisional application No. 62/262,542, filed on Dec. 3, 2015.

(51) Int. Cl.
C07C 37/00 (2006.01)
C07C 37/08 (2006.01)
(Continued)

(52) U.S. Cl.
CPC ............ *C07C 37/005* (2013.01); *C07C 37/08* (2013.01); *C07C 37/20* (2013.01); *C07C 37/685* (2013.01);
(Continued)

(58) Field of Classification Search
CPC .................................................. C07C 37/005
(Continued)

(56) References Cited

U.S. PATENT DOCUMENTS 8,143,456 B2  3/2012  Young et al.
9,255,053 B2  2/2016  Palmer et al.
(Continued)

FOREIGN PATENT DOCUMENTS

JP  3775832 B2      4/1997
JP  3775832 B2 *  5/2006  ............. C07C 37/08

OTHER PUBLICATIONS

International Search Report for International Application No. PCT/IB2016/075024; International Filing Date Nov. 22, 2016; dated Mar. 6, 2017; 5 pages.
(Continued)

*Primary Examiner* — Deborah D Carr
(74) *Attorney, Agent, or Firm* — Cantor Colburn LLP (57) ABSTRACT

In an embodiment, a method of recovering an unreacted phenol from a bisphenol A production facility comprises reacting an initial phenol and an initial acetone in the presence of a catalyst to produce a bisphenol A stream comprising the unreacted phenol of the initial phenol and a bisphenol A, separating a purge stream comprising the unreacted phenol, and wherein the unreacted phenol is present in the purge stream in an amount of 60 to 90 wt %, based on the total weight of the purge stream; adding the purge stream to a phenol purification section of a phenol production facility; and forming a purified phenol outlet
(Continued)

stream in the phenol purification section, wherein the purified phenol outlet stream comprises a total phenol concentration of greater than or equal to 99.5 wt % based on the total weight of the purified phenol outlet stream.

17 Claims, 2 Drawing Sheets (51) Int. Cl.
    *C07C 37/20*     (2006.01)
    *C07C 37/68*     (2006.01)
    *C07C 37/74*     (2006.01)
    *C07C 37/80*     (2006.01)
    *C07C 37/84*     (2006.01)
    *C07C 39/04*     (2006.01)
    *C07C 39/16*     (2006.01)

(52) U.S. Cl.
    CPC .............. *C07C 37/74* (2013.01); *C07C 37/80* (2013.01); *C07C 37/84* (2013.01); *C07C 39/04* (2013.01); *C07C 39/16* (2013.01)

(58) Field of Classification Search
    USPC .......................................................... 568/749
    See application file for complete search history.

(56) References Cited

U.S. PATENT DOCUMENTS

| | | |
|---|---|---|
| 2004/0249224 A1 | 12/2004 | Kumbhar et al. |
| 2008/0281129 A1 | 11/2008 | Palmer |
| 2010/0105960 A1 | 4/2010 | Evitt et al. |
| 2014/0121417 A1 | 5/2014 | Youssef et al. |
| 2017/0240496 A1 | 8/2017 | Nelson et al. |
| 2018/0230075 A1 | 8/2018 | Nelson et al. |

OTHER PUBLICATIONS

Noureldin et al.; "Global energy targets and optimal operating conditions for waste energy recovery in Bisphenol-A plant"; Applied Thermal Engineering 26 (2006); pp. 374-381.

Written Opinion of the International Search Report for International Application No. PCT/IB2016/075024; International Filing Date Nov. 22, 2016; dated Mar. 6, 2017; 7 pages.

* cited by examiner

METHOD OF RECOVERING PHENOL FROM A BPA PRODUCTION FACILITY AND THE FACILITY FOR RECOVERING THE SAME

CROSS REFERENCE TO RELATED APPLICATIONS

This application is a National Stage application of PCT/IB2016/057024, filed on Nov. 22, 2016, which claims the benefit of U.S. Provisional Application No. 62/262,542, filed Dec. 3, 2015, both of which are incorporated by reference in their entirety herein.

TECHNICAL FIELD

This disclosure relates to a method of recovering phenol in a BPA production facility and the facility for recovering the same.

BACKGROUND

Bisphenol A (BPA) is a high production volume compound with a world-wide estimated annual production of over 2 million tons. The demand for this compound is primarily due to its use as a monomer in the production of many high commodity materials such as epoxies and polycarbonates. The general process by which BPA is produced involves the condensation reaction of acetone with two equivalents of phenol in the presence of an acid catalyst or a sulfonated polystyrene resin. This reaction is often performed in an excess of phenol in order to help ensure full condensation. As a result, in a BPA production facility, the product stream comprises the excess phenol that can be separated from the product BPA. This excess unreacted phenol can be recovered and either recycled back to the BPA production facility or used for a different process.

There remains a need in the art for a process, which can more efficiently recover phenol from a BPA facility.

BRIEF SUMMARY

Disclosed herein is a method of recovering phenol in a BPA production facility and the facility for recovering the same.

In an embodiment, a method of recovering an unreacted phenol from a bisphenol A production facility comprises reacting an initial phenol and an initial acetone in the presence of a catalyst to produce a bisphenol A stream comprising the unreacted phenol of the initial phenol and a bisphenol A, separating a purge stream comprising the unreacted phenol, and wherein the unreacted phenol is present in the purge stream in an amount of 60 to 90 wt %, based on the total weight of the purge stream; adding the purge stream to a phenol purification section of a phenol production facility; and forming a purified phenol outlet stream in the phenol purification section, wherein the purified phenol outlet stream comprises a total phenol concentration of greater than or equal to 99.5 wt % based on the total weight of the purified phenol outlet stream.

In another embodiment, a system for recovering phenol comprises a bisphenol A production facility in fluid communication with a phenol purification section of a phenol production facility. The phenol purification section comprises a preheater comprising a preheater inlet and a preheater outlet, a splitter column comprising a splitter inlet in fluid communication with the preheater outlet, a splitter top outlet, and a splitter bottom outlet, a crude phenol column comprising a crude inlet in fluid communication with the splitter bottom outlet, a crude top outlet, and a crude bottom outlet, a hydro-extractor column comprising an extractor inlet in fluid communication with the crude top outlet, an extractor outlet, and an extractor primary outlet, and a finishing column comprising a finisher inlet in fluid communication with the extractor primary outlet, a product phenol outlet, and a finisher bottom outlet. The bisphenol A production facility comprising a bisphenol A reactor comprising a bisphenol A reactor inlet and a bisphenol A reactor outlet; a crystallization unit comprising a crystallization inlet and a crystallization outlet; wherein the crystallization inlet is in fluid communication with the bisphenol A reactor outlet; a melting unit comprising a melting unit inlet and a melting unit outlet; wherein the melting unit inlet is in fluid communication with the crystallization outlet; a filter comprising a filter inlet and a filter outlet; wherein the filter inlet is in fluid communication with the melting unit outlet; and a water stripper comprising a filtered stream inlet, a water stream outlet, and an unreacted phenol stream outlet; wherein the filtered stream inlet is in fluid communication with the filter outlet. The unreacted phenol stream outlet of the bisphenol A production facility is in intermittent fluid communication or is in constant fluid communication with the phenol purification section; and wherein the system is configured such that a purge stream exiting the unreacted phenol stream outlet comprises 60 to 90 wt % of an unreacted phenol based on the total weight of the purge stream.

The above described and other features are exemplified by the following figures and detailed description.

BRIEF DESCRIPTION OF THE DRAWINGS

Refer now to the figures, which is an exemplary embodiment. It is noted that the streams entering each of the respective columns can enter as separate streams or as combined streams and that the figures are merely illustrations of embodiments of the present disclosure.

DETAILED DESCRIPTION

Phenol purification from a typical BPA production facility generally results in a maximum phenol purity of 99 weight percent (wt %), more specifically, a maximum of 98 wt % based on the total weight of the purified stream. It was unexpectedly discovered that the capability of the phenol purification section of a phenol production facility can be advantageously used to purify the unreacted phenol present in a purge stream from a BPA production facility. The purge stream can be any stream removed from a BPA production facility comprising 60 to 90 wt %, specifically, 75 to 90 wt % phenol, more specifically, 75 to 85 wt % of phenol. The purge stream can be in at least intermittent fluid communication with the phenol purification section of the phenol production facility, for example the purge stream can be in constant fluid communication with the phenol purification section of the phenol production facility. The benefits of purifying the purge stream from the BPA production facility in a phenol purification section of a phenol production facility arise from the fact that the phenol purification section of the phenol production facility has a significantly greater throughput than that of a typical phenol purification section of a BPA production facility, for example, of only 55 to 76 tons per year. Due to the increased throughput in the phenol purification section of the phenol production facility, the phenol purification can achieve a greater operating efficiency then a phenol purification section of a BPA production facility. For example, the purification section of the phenol production facility can achieve a higher phenol purification to result in a phenol product comprising greater than or equal to 99 to 100 wt %, specifically 99.5 to 100 wt %, specifically, 99.9 to 100 wt % based on the total weight of the phenol product stream. Thus, the operational and capital cost of these purification facilities can be reduced without negatively affecting the quality of the product streams generated in the facilities.

Figure 1:
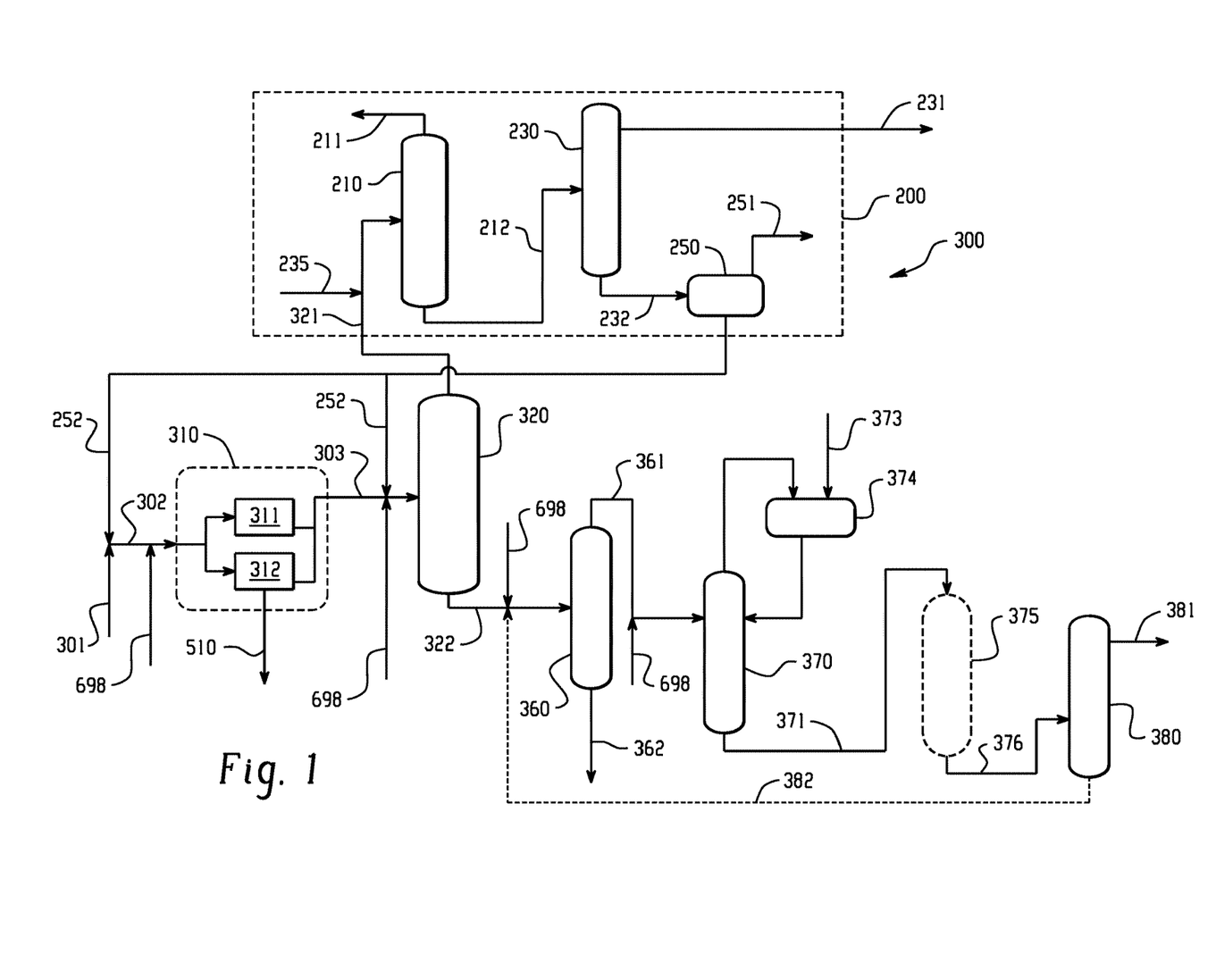
FIG. 1 is a schematic illustration of an embodiment of a phenol purification section of a phenol production facility.

An example of a reaction to produce phenol is via the cumene process. Here, a reaction mixture of benzene, propylene, and oxygen is reacted to produce a product mixture comprising acetone and phenol. A phenol purification section used to purify the production mixture comprising the acetone and the phenol can also be used to purify a purge stream comprising an unreacted phenol from a BPA production facility. Such a purification is illustrated in FIG. 1. FIG. 1 is a schematic illustration of a phenol purification section 300 of a phenol production facility. The phenol purification section 300 can include a feed stream 301 comprising acetone and phenol. The feed stream 301 can be in fluid communication with a phenol reactor, for example, such that an outlet stream from the phenol reactor is feed stream 301. The feed stream 301 can further comprise non-phenol compounds from upstream phenol production processes such as water, cumene, dimethylbenzyl alcohol (DMBA), hydroxyacetone (HA), α-methylstyrene (AMS), AMS dimers, acetophenone (AP), acetaldehyde, cumyl phenols, phenolic resins, or a combination including at least one of the foregoing.

The feed stream 301 can be combined with one or both of an acetone purification recycle stream 252 containing phenol recovered from an acetone purification section 200 and purge stream 698 to form a preheater inlet stream 302. The preheater inlet stream 302 can be heated in a preheater 310 by any suitable heating process. For example, preheater 310 can comprise preheater units 311 and 312 that operate in parallel. In this configuration, the preheater 310 can accommodate a higher flowrate while still heating the preheater inlet stream 302 to a desired temperature. It is noted that while it is illustrated that the three streams are combined prior to entering the preheater, the streams can be added in other configurations to the preheater.

The preheater 310 can be in fluid communication with a splitter column 320 via splitter inlet stream 303. Splitter inlet stream 303 can comprise 5 to 50 wt %, specifically, 10 to 40 wt %, more specifically, 20 to 30 wt % acetone. Splitter inlet stream 303 can comprise 20 to 75 wt %, specifically, 30 to 60 wt %, more specifically, 40 to 50 wt % phenol. The splitter inlet stream 303 can comprise 0 to 35 wt %, specifically, 5 to 30 wt % of a non-phenol compound. The preheater can be operated such that the splitter inlet stream 303 is heated to a temperature of greater than or equal to 90° C., for example, 90 to 180° C., or 90 to 150° C., or 100 to 135° C. One or both of an acetone purification recycle stream 252 and purge stream 698 can be added to the splitter inlet stream 303 prior to entering the splitter column 320, or can be added separately. The splitter column 320 separates species of the splitter inlet stream 303 into a splitter top outlet stream 321 and a splitter bottom outlet stream 322 based on their volatility (e.g., the tendency of the species to vaporize at a given temperature which is related to the species vapor pressure). The splitter column 320 can include one or more distillation columns. The splitter column 320 can operate at a temperature of 90 to 150 degrees Celsius (° C.), specifically, 100 to 140° C. The splitter column 320 can operate at a pressure of 250 to 450 kilopascal (kPa), specifically, 300 to 400 kPa.

The splitter top outlet stream 321 can contain the high volatility species of the splitter inlet stream 303 including acetone. The splitter top outlet stream 321 can comprise 30 to 70 wt %, specifically, 40 to 60 wt % acetone. The splitter top outlet stream 321 can comprise 0 to 5 wt %, specifically, 0 to 1 wt % phenol. The splitter top outlet stream 321 can comprise 30 to 70 wt %, specifically, 40 to 60 wt % of non-phenol compounds such as cumene, α-methylstyrene, water, hydroxyacetone, acetaldehyde, or a combination comprising at least one of the foregoing. The splitter top outlet stream 321 can comprise 0 to 1 wt % of each of the following independently: dimethylbenzyl alcohol, paracumyl phenol, dicumyl phenol, hydroxyacetone, acetophenone, methanol, acetaldehyde, AMS dimer, and 2-methylbenzofuran.

The splitter top outlet stream 321 can be recovered from the top of the splitter column 320 and fed to the acetone purification section 200 where an acetone product stream 231 can be recovered. The acetone product stream 231 can comprise greater than or equal to 95 wt % acetone, or 95 to 100 wt %, or, 97 to 99.99 wt %. The acetone purification section 200 can provide the acetone purification recycle stream 252 comprising phenol which can be combined with the feed stream 301, combined with the splitter inlet stream 303, sent to a separate process, or a combination including at least one of the foregoing.

A splitter bottom outlet stream 322 can be recovered from the bottom of the splitter column 320. The splitter bottom outlet stream 322 can comprise lower volatility species of the splitter inlet stream 303 including phenol. The splitter bottom outlet stream 322 can comprise greater than or equal to 94 wt %, specifically, 95 to 99 wt %, more specifically, 97 to 99 wt % of phenol. The splitter bottom outlet stream 322 can comprise 0 to 4 wt % of α-methylstyrene. The splitter bottom outlet stream 322 can comprise 0 to 2 wt % of acetophenone. The splitter bottom outlet stream 322 can comprise 0 to 1 wt % of each of the following independently: acetone, cumene, α-methylstyrene, water, dimethylbenzyl alcohol, paracumyl phenol, dicumyl phenol, hydroxyacetone, acetophenone, methanol, acetaldehyde, 2-methylbenzofuran, and AMS dimers.

The splitter bottom outlet stream 322 can be fed to a crude phenol column 360 where it can be separated into a crude top outlet stream 361 and a crude bottom outlet stream 362. The crude phenol column inlet stream can include the splitter bottom outlet stream 322, an optional finisher bottom outlet stream 382, or a combination including at least one of the foregoing. The crude phenol column 360 can operate at a temperature of 100 to 300° C., specifically, 150 to 250° C. The crude phenol column 360 can operate at a pressure of 75 to 275 kPa, specifically, 100 to 225 kPa. The crude phenol column 360 can include a distillation column which can separate species present in the splitter bottom outlet stream 322 based on their volatility.

The crude bottom outlet stream 362 can include lower volatility species present in the splitter bottom outlet stream 322 such as paracumyl phenol, dicumyl phenol, AP, AMS dimer, or a combination comprising at least one of the foregoing. For example, the crude bottom outlet stream 362 can contain dimethylbenzyl alcohol, acetophenone, AMS dimers, dicumyl phenol, paracumyl phenol (PCP), or a combination comprising at least one of the foregoing. The crude bottom outlet stream 362 can be recovered from the phenol purification section 300 for separate processing. The crude top outlet stream 361 can comprise 97 to 99.7 wt % of phenol.

The crude top outlet stream 361 can be fed to an extractor inlet of a hydro-extractor column 370. Water stream 373 containing water can be fed directly to the hydro-extractor column 370 or to a cooler 374 in fluid communication with the hydro-extractor column 370. The hydro-extractor column 370 can include a liquid-liquid extraction device, which can separate compounds based on their relative solubilities in two different immiscible liquid phases. Non-phenol compounds present in one liquid phase (e.g., a phenol rich phase) can be extracted to a second liquid phase (e.g., a water phase) where the non-phenol compound has a greater solubility. Water stream 373 can be used to extract non-phenol compound (e.g., alkylated benzenes) present in the crude top outlet stream 361.

The hydro-extractor column 370 can include internal structures to increase the interfacial area between the two liquid phases. These internal structures can include fixed plates, packing, or a combination including at least one of the foregoing. The hydro-extractor column 370 can be heated (e.g., through a heat exchanger in thermal communication with the hydro-extractor column 370). The hydro-extractor can operate in any suitable flow configuration such that interaction between the two immiscible liquid phases is ensured. For example, heat supplied to the hydro-extractor can buoy the water phase and drive counter-current flow of the two liquid phases within the hydro-extractor, where the phenol rich phase moves toward the bottom of the hydro-extractor while the water phase moves towards the top. The water phase can be cooled in the cooler 374 and returned to the hydro-extractor.

The hydro-extractor column 370 can operate at a temperature of 30 to 100° C., specifically, 50 to 70° C. The hydro-extractor column 370 can operate at a pressure of 350 to 550 kPa, specifically, 400 to 500 kPa. At least a portion of the top stream exiting the hydro-extractor column 370 can be removed from the system, for example, upstream of or downstream of the cooler 374 and can optionally be recycled to an upstream unit such as one or both of splitter column 320 or crude phenol column 360.

The extractor primary outlet stream 371 can include the phenol rich phase including phenol and non-phenol compounds (e.g., dicumyl phenol, 2-methylbenzofuran (2-MBF), AP, or a combination comprising at least one of the foregoing). The extractor primary outlet stream 371 can comprise 98 to 99.999 wt % of phenol. Non-phenol compounds present in the extractor primary outlet stream 371 can include heteroatoms (e.g., 2-MBF) which can be alkylated to higher molecular mass species (e.g., greater molecular mass in comparison to the species having the heteroatom) in an optional ion exchanger 375. The effluent from the optional ion exchanger 375 can be fed along a finisher inlet stream 376 to a finishing column 380.

The finishing column 380 can separate the finisher inlet stream 376 into a purified phenol outlet stream 381 and a finisher bottom outlet stream 382. The finisher bottom outlet stream 382 can optionally be recycled and combined with the splitter bottom outlet stream 322. The finisher column 380 can include at least one distillation column. The purified phenol outlet stream 381 can be recovered from the phenol purification section 300 and used in the manufacture of bisphenol-A (BPA) in a BPA production facility. The purified phenol outlet stream 381 can comprise greater than or equal to 99.5 wt %, specifically, 99.5 to less than 100 wt % of phenol.

The phenol purification section 300 can further comprise an acetone purification section 200, where the splitter top outlet stream 321 can be purified in the acetone purification section 200. For example, the splitter top outlet stream 321 and caustic stream 235 can be added to a first acetone column 210 to form a first top stream 211 and a first bottom stream 212 comprising a purified acetone. The first bottom stream 212 can be added to a second acetone column 230 to form a second bottom stream 232 and acetone product stream 231 comprising the purified product acetone. The acetone product stream 231 can comprise 99.5 to 99.9 wt % of acetone. The acetone product stream 231 can comprise less than or equal to 0.5 wt % of water. The second bottom stream 232 can be separated in a separator 250, for example, in a decanter, to form decanted stream 251 comprising cumene and an acetone phenol recycle stream 252 that can be added to one or both of the preheater 310 and to the splitter column 320.

The purge stream 698 can be combined with the phenol purification section 300 can be combined with at least one of the preheater inlet stream 302, the splitter inlet stream 303, the splitter bottom outlet stream 322, and the crude top outlet stream 361.

Combining the purge stream 698 and the preheater inlet stream 302 can allow the streams to equilibrate prior to entering the splitter column 320. The preheater 310 can be a more efficient heat transfer device in comparison to the splitter column 320 (e.g., owed to lower heat loss, lower thermal resistance of the material of construction, or flow configuration), or the opposite can be the case. Thus, selecting between the preheater inlet stream 302 and the splitter inlet stream 303, or selecting how much of the purge stream 698 is supplied to either location, can be influenced by heat transfer efficiency differences between the preheater 310 and the splitter column 320. It is noted that if the purge stream 698 is added to the preheater 310 a water removal stream 510 can be added to remove an amount of water above an equilibrium amount.

Combining the purge stream 698 downstream of the splitter column 320, for example, with one or both of the splitter bottom outlet stream 322 and crude top outlet stream 361 can reduce or eliminate the possibility that non-phenol compounds are transferred from the BPA production facility to the acetone product stream 231. Combining the purge stream 698 with the extractor inlet stream (crude top outlet stream 361) can require less energy to heat the purge stream 698 in comparison to the other locations to which the purge stream can be fed (e.g., the preheater inlet stream 302, the splitter inlet stream 303, or the crude phenol column 360 inlet).

The phenol recovery of an unreacted phenol from a BPA production facility can be done in a phenol recovery section of a phenol production facility. For example, the phenol purification section 300 that purifies phenol produced in a phenol production facility can purify a purge stream from a bisphenol-A production facility. The phenol purification section 300 can comprise a preheater 310, a splitter column 320, a crude phenol column 360, a hydro-extractor column 370, an optional ion exchanger 375, and a finishing column 380. The preheater 310 can comprise a preheater inlet and a preheater outlet. The splitter column 320 can comprise a splitter inlet in fluid communication with the preheater outlet, a splitter top outlet, and a splitter bottom outlet. The crude phenol column 360 can comprise a crude inlet in fluid communication with the splitter bottom outlet, a crude top outlet, and a crude bottom outlet. The hydro-extractor column 370 can comprise an extractor inlet in fluid communication with the crude top outlet, an extractor outlet, and an extractor primary outlet. The hydro-extractor column 370 can comprise a cooler extractor inlet that can be in fluid communication with a cooler outlet of a cooler 374. The cooler 374 can further comprise a cooler inlet in fluid communication with the extractor outlet. The finishing column 380 can comprise a finisher inlet in fluid communication with the extractor primary outlet, a product phenol outlet, and a finisher bottom outlet. The finisher bottom outlet can optionally be in fluid communication with the crude inlet. The system can optionally comprise an optional ion exchanger 375 comprising an exchanger inlet in fluid communication with the extractor primary outlet and an exchanger outlet in fluid communication with the finisher inlet.

The acetone purification section 200 can comprise first acetone column 210, second acetone column 230, and separator 250. First acetone column 210 can comprise a first acetone inlet, a first acetone top outlet, and a first acetone bottom outlet. Second acetone column 230 can comprise a second acetone inlet, a second acetone top outlet, and a second acetone bottom outlet. Separator 250 can comprise a separator inlet, a separator top outlet, and a separator bottom outlet. The first acetone bottom outlet can be in fluid communication with the second acetone inlet. The second acetone bottom outlet can be in fluid communication with the separator inlet. The separator bottom outlet can be in fluid communication with the preheater inlet.

Figure 2:
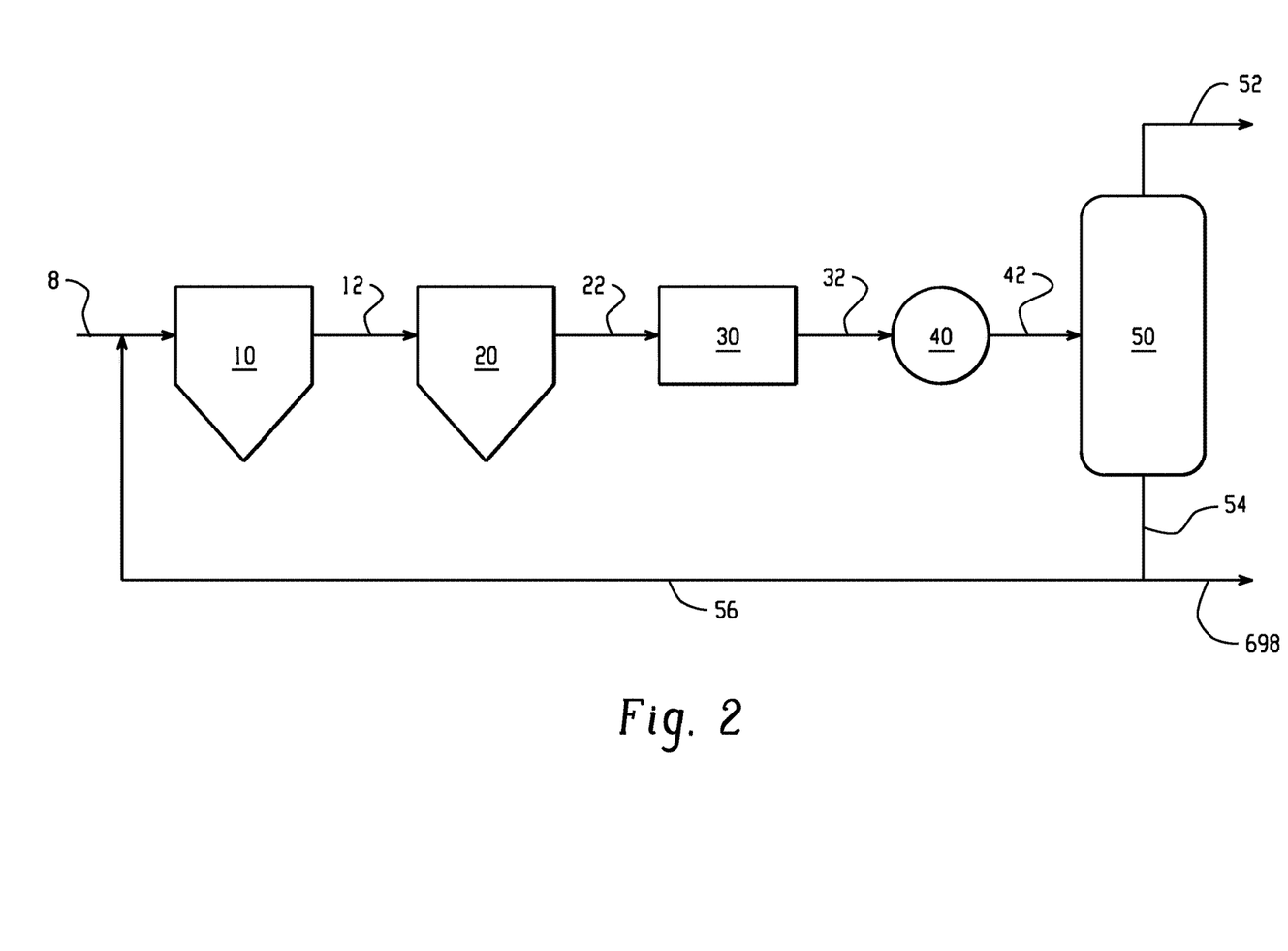
FIG. 2 is a schematic illustration of an embodiment of a bisphenol A production facility.

A bisphenol A production facility is illustrated in FIG. 2. FIG. 2 illustrates that reactor feed stream 8 can be directed to the BPA reactor 10 to form BPA stream 12. Reactor feed stream 8 can comprise phenol, acetone, and optionally a promoter. The reactor can be a fixed bed reactor comprising a catalyst. The catalyst can comprise an ion exchange resin (such as a tert-amine divinylbenzene/styrene ion exchange copolymer). The catalyst can comprise a strong acid catalyst (such as hydrochloric acid), a sulfonic resin and a sulfur containing promoter (such as a mercaptan promoter (such as methyl mercaptan, ethyl mercaptan, 2,2-bis(methylthio)propane, mercaptocarboxylic acid, and 3-mercaptopropionic acid), as well as combinations comprising at least one of the foregoing. The phenol and acetone can be present in a molar ratio of 2:1 to 5:1. Reactor feed stream 8 can comprise 75 to 95 wt % phenol and 3 to 25 wt % acetone. The phenol and acetone can be combined in a formulation tank located upstream of BPA reactor 10. BPA stream 12 can be removed from BPA reactor 10. BPA stream 12 can comprise 10 to 50 wt % of bisphenol A.

BPA stream 12 can be directed to crystallization unit 20 to form BPA crystals comprising, for example, one or both of crystalline BPA and an adduct of BPA and phenol. It is noted that "adduct" as used herein refers to the physical association of BPA and phenol (e.g., one molecule of BPA and one molecule of phenol can crystallize together to form a 1:1 molar ratio of BPA/phenol adduct). The crystallization can occur via cooling of the BPA stream. Water can be added to the crystallization unit 20 to increase the rate of the crystallization. The water can be present in BPA stream 12 in an amount of less than or equal to 3 wt %, specifically, 0.1 to 3 wt %. The crystals can be separated by removing the solid portion from the crystallization unit comprising the crystals, for example, via filtration, to form crystallized stream 22.

Crystallized stream 22 can be directed to melting unit 30. The melting unit 30 can melt the crystals, for example, by heating the crystals at a temperature greater than or equal to the crystallization temperature. An additional amount of phenol can be added to the crystallized stream 22 to facilitate the melting of the crystals at a lower temperature. The temperature of the melting unit 30 can be 70 to 100° C., specifically, 75 to 90° C. The crystals can be melted in melting unit 30 to form a melt comprising bisphenol A and phenol. When the melt comprises sulfur, then a base (such as sodium hydroxide and potassium hydroxide) can be added to the melt to form a melt stream with a reduced sulfur content. Melted stream 32 can be directed to filter 40 to form a bisphenol A stream (not shown) and filtered stream 42 comprising 60 to 90 wt % phenol, 5 to 20 wt % bisphenol A, and 5 to 20 wt % water. Filter 40 can comprise a rotary vacuum filter. The bisphenol A stream can be further purified to produce a product bisphenol A. The product bisphenol A can be solidified, for example, in a flaking unit, not shown in FIG. 2.

Filtered stream 42 can be directed to water stripper 50 to form water stream 52 and unreacted phenol stream 54. Water stream 52 can comprise greater than or equal to 25 wt % water, for example, 30 to 80 wt % water. Unreacted phenol stream 54 can comprise 60 to 90 wt % phenol, specifically, 75 to 90 wt % phenol, more specifically, 75 to 85 wt % phenol. All or a portion of unreacted phenol stream 54 can be directed to the phenol purification facility as purge stream 698. Purge stream 698 can comprise 60 to 90 wt % phenol, specifically, 75 to 90 wt % phenol, more specifically, 75 to 85 wt % phenol. A recycle portion of unreacted phenol stream 54 can be directed to BPA reactor 10 as recycle stream 56.

The amount of unreacted phenol stream 54 that is purified can be determined by first determining an acceptable impurity level that can be present in the BPA reaction, determining an actual impurity level present in the BPA reaction, and determining a recycle amount of the unreacted phenol stream to be directed to the BPA reaction and a purification amount of unreacted phenol stream 54 to be directed as purge stream 698 to the phenol purification section of the phenol production facility. For example, if the impurity level in the BPA reactor is greater than the acceptable impurity, then less of unreacted phenol stream 54 can be directed as recycle stream 56 to the BPA reactor and, for example, more of the unreacted phenol stream 54 can be directed as purge stream 698 to the phenol purification section of the phenol production facility. If the impurity level in the BPA reactor is less than or equal the acceptable impurity level, then the amount of unreacted phenol stream 54 that is being directed to the BPA reactor as recycle stream 56 can be maintained or increased and the purification amount that is being directed as purge stream 698 to the phenol purification section of the phenol production facility can be maintained or can be reduced. The amount of unreacted phenol stream 54 that is directed as purge stream 698 to the phenol purification section 300 can be 2 to 90 wt %, specifically, 2 to 50 wt %, more specifically, 3 to 20 wt %, still more specifically, 4 to 15 wt % of the total amount of unreacted phenol stream 54.

The purge stream 698 can be combined with the preheater inlet stream 302, the splitter inlet stream 303, the splitter bottom outlet stream 322, and the crude top outlet stream 361, or a combination comprising at least one of the foregoing. A water stripper bottom outlet can be in fluid communication with one or more of preheater 310, splitter column 320, crude phenol column 360, and hydro-extractor column 370.

A storage tank can optionally be located downstream of the water stripper and upstream of the phenol purification facility. For example, the purge stream can be directed to a storage tank or unreacted phenol stream can be directed to the storage tank such that the unreacted phenol stream and the purge stream are removed from the storage tank. The storage tank can be stationary or can be mobile such that the storage tank can deliver the water stripper bottom mixture from the BPA production facility to the phenol purification facility. In other words, an unreacted phenol stream outlet of the water stripper can be in intermittent fluid communication (for example, the storage tank can be a mobile storage to move the fluid across a distance from the BPA production facility to the phenol production facility) or in constant fluid communication with phenol purification facility. No separation unit can be located in between the water stripper bottom outlet and the phenol purification section 300. The first separation unit that the purge stream can encounter can be a separation unit in the phenol purification section 300.

Set forth below are some embodiments of the present method of purifying an unreacted phenol and a system for purifying the same.

Embodiment 1

A method of recovering an unreacted phenol from a bisphenol A production facility comprising: reacting an initial phenol and an initial acetone in the presence of a catalyst to produce a bisphenol A stream comprising the unreacted phenol of the initial phenol and a bisphenol A, separating a purge stream comprising the unreacted phenol, and wherein the unreacted phenol is present in the purge stream in an amount of 60 to 90 wt %, based on the total weight of the purge stream; adding the purge stream to a phenol purification section of a phenol production facility; and forming a purified phenol outlet stream in the phenol purification section, wherein the purified phenol outlet stream comprises a total phenol concentration of greater than or equal to 99.5 wt % based on the total weight of the purified phenol outlet stream.

Embodiment 2

The method of Embodiment 1, wherein the forming the purified phenol outlet stream comprises: heating a preheater inlet stream comprising cumene, a product phenol from the phenol production facility, and a product acetone from the phenol production facility in a preheater to form a splitter inlet stream; separating the splitter inlet stream into a splitter top outlet stream comprising the product acetone and the cumene and a splitter bottom outlet stream comprising the product phenol in a splitter column; separating the splitter bottom outlet stream into a crude top outlet stream comprising the product phenol and a crude bottom outlet stream comprising the cumene in a crude phenol column; hydro-extracting the crude top outlet stream in a hydro-extractor column to form an extractor primary outlet stream comprising the product phenol; and recovering the purified phenol outlet stream, from the extractor primary outlet stream in a finishing column; wherein the adding the purge stream comprises adding the purge stream to one or more of the preheater inlet stream, the splitter inlet stream; the splitter bottom outlet stream; and the crude top outlet stream.

Embodiment 3

The method of Embodiment 2, further comprising purifying the splitter top outlet stream and forming an acetone product stream comprising the product acetone.

Embodiment 4

The method of any one of the preceding embodiments, wherein the separating the purge stream comprises: crystallizing the bisphenol A in the bisphenol A stream in the presence of water to form crystals comprising one or both of crystalline bisphenol A and an adduct of bisphenol A and the unreacted phenol; forming a crystallized stream; melting the crystallized stream to form a melted stream; filtering the melted stream to form a filtered stream; removing the water from the filtered stream in a water stripper to form water stream and an unreacted phenol stream; wherein the purge stream comprises all or a portion of the unreacted phenol stream.

Embodiment 5

The method of Embodiment 4, wherein the water is present an amount of less than or equal to 3 wt % based on the total weight of the bisphenol A stream.

Embodiment 6

The method of any one of Embodiments 4-5, wherein the forming a crystallized stream comprises filtering a solid portion comprising the crystals.

Embodiment 7

The method of any one of Embodiments 4-6, further comprising adding additional phenol to the crystallized stream prior to the melting.

Embodiment 8

The method of any one of Embodiments 4-7, wherein the filtering the melted stream comprises filtering in a rotary vacuum filter.

Embodiment 9

The method of any one of the preceding embodiments, further comprising directing at least a portion of the purified phenol outlet stream to one or both of the bisphenol A production facility and a diphenyl carbonate production facility.

Embodiment 10

The method of any one of the preceding embodiments, further comprising: determining an acceptable impurity level that can be present during the reacting of the initial phenol and the initial acetone; determining an actual impurity level present in the reacting of the initial phenol and the initial acetone; based on the acceptable impurity level and the actual impurity level, determining a recycle amount of an unreacted phenol stream to be recycled to the bisphenol A production facility and a purification amount to be directed as the purge stream to the phenol purification facility;

directing the purification amount of the purge stream to the phenol purification facility; and directing the recycle amount to a bisphenol A reactor.

Embodiment 11

The method of any one of the preceding embodiments, wherein the purified phenol outlet stream comprises less than or equal to 0.001 wt % of each independently or of a combined amount of water, cumene, dimethylbenzyl alcohol, hydroxyacetone, α-methylstyrene, α-methylstyrene dimers, acetophenone, acetaldehyde, cumyl phenols, and phenolic resins based on the total weight of the purified phenol outlet stream.

Embodiment 12

The method of any one of the preceding embodiments, wherein the separating the purge stream comprises removing the purge stream from a storage tank prior to adding the purge stream to the phenol purification section of the phenol production facility.

Embodiment 13

The method of Embodiment 12, wherein the storage tank is in intermittent fluid communication or is in continuous fluid communication with the phenol purification section.

Embodiment 14

A system for recovering phenol comprising: a bisphenol A production facility in fluid communication with a phenol purification section of a phenol production facility. The phenol purification section comprises a preheater comprising a preheater inlet and a preheater outlet, a splitter column comprising a splitter inlet in fluid communication with the preheater outlet, a splitter top outlet, and a splitter bottom outlet, a crude phenol column comprising a crude inlet in fluid communication with the splitter bottom outlet, a crude top outlet, and a crude bottom outlet, a hydro-extractor column comprising an extractor inlet in fluid communication with the crude top outlet, an extractor outlet, and an extractor primary outlet, and a finishing column comprising a finisher inlet in fluid communication with the extractor primary outlet, a product phenol outlet, and a finisher bottom outlet. The bisphenol A production facility comprising a bisphenol A reactor comprising a bisphenol A reactor inlet and a bisphenol A reactor outlet; a crystallization unit comprising a crystallization inlet and a crystallization outlet; wherein the crystallization inlet in in fluid communication with the bisphenol A reactor outlet; a melting unit comprising a melting unit inlet and a melting unit outlet; wherein the melting unit inlet is in fluid communication with the crystallization outlet; a filter comprising a filter inlet and a filter outlet; wherein the filter inlet is in fluid communication with the melting unit outlet; and a water stripper comprising a filtered stream inlet, a water stream outlet, and an unreacted phenol stream outlet; wherein the filtered stream inlet is in fluid communication with the filter outlet. The unreacted phenol stream outlet of the bisphenol A production facility is in intermittent fluid communication or is in constant fluid communication with the phenol purification section; and wherein the system is configured such that a purge stream exiting the unreacted phenol stream outlet comprises 60 to 90 wt % of an unreacted phenol based on the total weight of the purge stream.

Embodiment 15

The system of Embodiment 14, wherein the phenol purification section further comprises: a crude phenol column comprising a crude inlet in fluid communication with the splitter bottom outlet, a crude top outlet, and a crude bottom outlet, a hydro-extractor column comprising an extractor inlet in fluid communication with the crude top outlet, an extractor outlet, and an extractor primary outlet, and a finishing column comprising a finisher inlet in fluid communication with the extractor primary outlet, a product phenol outlet, and a finisher bottom outlet.

Embodiment 16

The system of Embodiment 15, further comprising an ion exchanger comprising an exchanger inlet in fluid communication with the extractor primary outlet and an exchanger outlet in fluid communication with the finisher inlet.

Embodiment 17

The system of Embodiment 17, wherein the finisher bottom outlet is in fluid communication with the crude inlet.

Embodiment 18

The system of any one of Embodiments 14-17, wherein the unreacted phenol stream outlet of the bisphenol A production facility is in fluid communication with the phenol purification section.

Embodiment 19

The system of any one of Embodiments 14-18, wherein the system is configured such that the purge stream entering the phenol purification section comprises 60 to 90 wt % of an unreacted phenol based on the total weight of the purge stream.

Embodiment 20

The system of any one of Embodiments 15-19, wherein the unreacted phenol stream outlet of the bisphenol A production facility is in fluid communication with the preheater inlet, the splitter inlet, the crude inlet, the extractor inlet, or a combination comprising at least one of the foregoing.

Although the description of the process is directed to a continuous process, any one or more of the steps can be conducted batch-wise.

It will be appreciated by persons skilled in the art that the positioning of the various streams/lines as described herein as being, e.g., in the "top", "middle", "bottom", or "side" of a particular vessel (such as an acid-cracker, distillation column, extraction column, and the like) is relative because the actual position at which material is to be introduced or recovered is dependent on the conditions being maintained in the particular unit. For example, a stream entering the "bottom" of a column can actually enter several stages above the sump including the reboiler of the column, and a stream exiting the "top" of the column can actually exit several stages below the top stage including the condenser of the column. Thus, such terms herein are included for ease of reference to describe a general orientation regarding various columns and lines/streams and such terms are not meant to be limiting to one exact location. Also, although for illustrative purposes, the accompanying figures depict singular units, it is understood that multiple vessels can be used where suitable. Furthermore, multiple vessels can have any suitable flow arrangement such as serial, parallel, or a combination including at least one of the foregoing.

Unless specifically stated otherwise, the weight percent values used herein are based on the total weight of the respective stream.

In general, the invention can alternately comprise, consist of, or consist essentially of, any appropriate components herein disclosed. The invention can additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. Unless otherwise stated, test standards are the most recent as of the filing date of the application. The present application claims the benefit of U.S. Prov. Application No. 62/262,542, filed on Dec. 3, 2015, and which is incorporated herein in its entirety.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

In addition, it is to be understood that the described elements can be combined in any suitable manner in the various embodiments.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

We claim:

1. A method of recovering an unreacted phenol from a bisphenol A production facility comprising:
    reacting an initial phenol and an initial acetone in the presence of a catalyst to produce a bisphenol A stream comprising the unreacted phenol of the initial phenol and a bisphenol A,
    separating a purge stream comprising the unreacted phenol, and wherein the unreacted phenol is present in the purge stream in an amount of 60 to 90 wt %, based on the total weight of the purge stream;
    adding the purge stream to a phenol purification section of a phenol production facility; and
    purifying the purge stream in the phenol purification section to form a purified phenol outlet stream in the phenol purification section, wherein the purified phenol outlet stream comprises a total phenol concentration of greater than or equal to 99.5 wt % based on the total weight of the purified phenol outlet stream.

2. The method of claim 1, wherein the forming the purified phenol outlet stream comprises:
    heating a preheater inlet stream comprising cumene, a product phenol from the phenol production facility, and a product acetone from the phenol production facility in a preheater to form a splitter inlet stream;
    separating the splitter inlet stream into a splitter top outlet stream comprising the product acetone and the cumene and a splitter bottom outlet stream comprising the product phenol in a splitter column;
    separating the splitter bottom outlet stream into a crude top outlet stream comprising the product phenol and a crude bottom outlet stream comprising the cumene in a crude phenol column;
    hydro-extracting the crude top outlet stream in a hydro-extractor column to form an extractor primary outlet stream comprising the product phenol; and
    recovering the purified phenol outlet stream, from the extractor primary outlet stream in a finishing column;
    wherein the adding the purge stream comprises adding the purge stream to one or more of the preheater inlet stream, the splitter inlet stream; the splitter bottom outlet stream; and the crude top outlet stream.

3. The method of claim 2, further comprising purifying the splitter top outlet stream and forming an acetone product stream comprising the product acetone.

4. The method of claim 1, wherein the separating the purge stream comprises:
    crystallizing the bisphenol A in the bisphenol A stream in the presence of water to form crystals comprising one or both of crystalline bisphenol A and an adduct of bisphenol A and the unreacted phenol;
    forming a crystallized stream comprising crystals;
    melting the crystallized stream to form a melted stream;
    filtering a solid portion comprising the crystals from the melted stream to form a filtered stream;
    removing the water from the filtered stream in a water stripper to form a water stream and an unreacted phenol stream;
    wherein the purge stream comprises all or a portion of the unreacted phenol stream.

5. The method of claim 4, wherein the water is present an amount of less than or equal to 3 wt % based on the total weight of the bisphenol A stream.

6. The method of claim 4, wherein the forming a crystallized stream comprises filtering a solid portion comprising the crystals.

7. The method of claim 4, further comprising adding additional phenol to the crystallized stream prior to the melting.

8. The method of claim 4, wherein the filtering the melted stream comprises filtering in a rotary vacuum filter.

9. The method of claim 1, further comprising directing at least a portion of the purified phenol outlet stream to one or both of the bisphenol A production facility and a diphenyl carbonate production facility.

10. The method of claim 1, further comprising:
determining an acceptable impurity level that can be present during the reacting of the initial phenol and the initial acetone;
determining an actual impurity level present in the reacting of the initial phenol and the initial acetone;
based on the acceptable impurity level and the actual impurity level, determining a recycle amount of an unreacted phenol stream to be recycled to the bisphenol A production facility and a purification amount to be directed as the purge stream to the phenol purification facility;
directing the purification amount of the purge stream to the phenol purification facility; and
directing the recycle amount to a bisphenol A reactor.

11. The method of claim 1, wherein the purified phenol outlet stream comprises less than or equal to 0.001 wt % of each independently water, cumene, dimethylbenzyl alcohol, hydroxyacetone, α-methylstyrene, α-methylstyrene dimers, acetophenone, acetaldehyde, cumyl phenols, and phenolic resins based on the total weight of the purified phenol outlet stream.

12. The method of claim 1, wherein the separating the purge stream comprises removing the purge stream from a storage tank prior to adding the purge stream to the phenol purification section of the phenol production facility.

13. The method of claim 12, wherein the storage tank is in intermittent fluid communication or is in continuous fluid communication with the phenol purification section.

14. A system for recovering phenol comprising:
a phenol purification section of a phenol production facility comprising
a preheater comprising a preheater inlet and a preheater outlet,
a splitter column comprising a splitter inlet in fluid communication with the preheater outlet, a splitter top outlet, and a splitter bottom outlet,
a crude phenol column comprising a crude inlet in fluid communication with the splitter bottom outlet, a crude top outlet, and a crude bottom outlet,
a hydro-extractor column comprising an extractor inlet in fluid communication with the crude top outlet, an extractor outlet, and an extractor primary outlet, and
a finishing column comprising a finisher inlet in fluid communication with the extractor primary outlet, a product phenol outlet, and a finisher bottom outlet; and
a bisphenol A production facility comprising
a bisphenol A reactor comprising a bisphenol A reactor inlet and a bisphenol A reactor outlet;
a crystallization unit comprising a crystallization inlet and a crystallization outlet; wherein the crystallization inlet in in fluid communication with the bisphenol A reactor outlet;
a melting unit comprising a melting unit inlet and a melting unit outlet; wherein the melting unit inlet is in fluid communication with the crystallization outlet;
a filter comprising a filter inlet and a filter outlet; wherein the filter inlet is in fluid communication with the melting unit outlet; and
a water stripper comprising a filtered stream inlet, a water stream outlet, and an unreacted phenol stream outlet; wherein the filtered stream inlet is in fluid communication with the filter outlet;
wherein a purge stream comprising at least a portion of the unreacted phenol stream outlet of the bisphenol A production facility is in intermittent fluid communication or is in constant fluid communication with the phenol purification section upstream of the finishing column; and wherein the system is configured such that the purge stream exiting the unreacted phenol stream outlet comprises 60 to 90 wt % of an unreacted phenol based on the total weight of the purge stream.

15. The system of claim 14, further comprising an ion exchanger comprising an exchanger inlet in fluid communication with the extractor primary outlet and an exchanger outlet in fluid communication with the finisher inlet and/or wherein the finisher bottom outlet is in fluid communication with the crude inlet.

16. The system of claim 14, wherein the unreacted phenol stream outlet of the bisphenol A production facility is in fluid communication with the preheater inlet, the splitter inlet, the crude inlet, the extractor inlet, or a combination comprising at least one of the foregoing.

17. A method of recovering an unreacted phenol from a bisphenol A production facility comprising:
reacting an initial phenol and an initial acetone in the presence of a catalyst to produce a bisphenol A stream comprising the unreacted phenol of the initial phenol and a bisphenol A;
separating a purge stream comprising the unreacted phenol; wherein the unreacted phenol is present in the purge stream in an amount of 60 to 90 wt %, based on the total weight of the purge stream; wherein the separating the purge stream comprises crystallizing the bisphenol A in the bisphenol A stream in the presence of water to form crystals comprising one or both of crystalline bisphenol A and an adduct of bisphenol A and the unreacted phenol, forming a crystallized stream, melting the crystallized stream to form a melted stream, filtering the melted stream to form a filtered stream, removing the water from the filtered stream in a water stripper to form a water stream and an unreacted phenol stream, wherein the purge stream comprises all or a portion of the unreacted phenol stream;
adding the purge stream to a phenol purification section of a phenol production facility; and
forming a purified phenol outlet stream in the phenol purification section, wherein the purified phenol outlet stream comprises a total phenol concentration of greater than or equal to 99.5 wt % based on the total weight of the purified phenol outlet stream;
wherein the forming the purified phenol outlet stream comprises heating a preheater inlet stream comprising cumene, a product phenol from the phenol production facility, and a product acetone from the phenol production facility in a preheater to form a splitter inlet stream;
separating the splitter inlet stream into a splitter top outlet stream comprising the product acetone and the cumene and a splitter bottom outlet stream comprising the product phenol in a splitter column; separating the splitter bottom outlet stream into a crude top outlet stream comprising the product phenol and a crude bottom outlet stream comprising the cumene in a crude phenol column; hydro-extracting the crude top outlet stream in a hydro-extractor column to form an extractor primary outlet stream comprising the product phenol; and recovering the purified phenol outlet stream, from the extractor primary outlet stream in a finishing column;

wherein the adding the purge stream comprises adding the purge stream to one or more of the preheater inlet stream, the splitter inlet stream; the splitter bottom outlet stream; and the crude top outlet stream.

* * * * *